(12) United States Patent
Morkin

(10) Patent No.: US 6,716,877 B2
(45) Date of Patent: Apr. 6, 2004

(54) METHOD TO TREAT CHRONIC HEART FAILURE AND/OR ELEVATED CHOLESTEROL LEVELS

(75) Inventor: Eugene Morkin, Tucson, AZ (US)

(73) Assignee: The Arizona Board of Regents on behalf of the University of Arizona, Phoenix, AZ (US)

( * ) Notice: Subject to any disclaimer, the term of this patent is extended or adjusted under 35 U.S.C. 154(b) by 72 days.

(21) Appl. No.: 10/368,755

(22) Filed: Feb. 18, 2003

(65) Prior Publication Data

US 2003/0147815 A1 Aug. 7, 2003

Related U.S. Application Data

(63) Continuation-in-part of application No. 09/774,994, filed on Jan. 31, 2001, now Pat. No. 6,534,676.

(51) Int. Cl.[7] .................. A61K 31/19; C07C 65/00; C07C 229/00
(52) U.S. Cl. .................. 514/557; 514/568; 562/405; 562/472; 562/447
(58) Field of Search .................. 562/405, 447, 562/472; 514/557, 568

(56) References Cited

U.S. PATENT DOCUMENTS

| | | | | |
|---|---|---|---|---|
| 3,109,023 | A | 10/1963 | Weil | 260/515 |
| 5,158,978 | A | * 10/1992 | Rubin | 514/567 |
| 5,284,971 | A | 2/1994 | Walker et al. | 562/429 |
| 5,883,294 | A | 3/1999 | Scanlan et al. | 562/471 |

OTHER PUBLICATIONS

Morken et al., "Studies on the Use of Thyroid Hormone and a Thyroid Hormone Analogue in the Treatment of Congestive Heart Failure", The Society of Thoracic Surgeons, 1993, Sections 54–60.
Pennock, et al., "Combination Treatment with Captopril and the Thyroid Hormone Analogue 3,5–Diiodothyropropionic Acid", Circulation, 1993, pp. 1289–1298.
Mahaffey, et al., "Left Ventricular Performance and Remodeling in Rabbits after Myocardial Infarction", American Heart Association, 1994, pp. 794–801.
Morkin, et al., "Development of a Thyroid Hormone Analogue for the Treatment of Congestive Heart Failure", Symposium on Novel Actions of Thyroid Hormone, 1996, pp. 521–526.
Spooner, et al., "Thyroid Hormone and Thyroid Hormone Analogues in the Treatment of Heart Failure", Lippincott Williams & Wilkins, 1999, pp. 395–399.
Pennock, et al., "Prevention of Abnormal Sarcoplasmic Reticulum Calcium Transport and Protein Expression in Post–infarction Heart Failure Using 3,5–Diiodothyropropionic Acid (DITPA)", Academic Press, 2000, pp. 1939–1953.

Deirdre M. B. Hickey et al., "Synthesis of Thyroid Hormone Analogues. Part. 3. Iodonium Salt Approaches to SK&F L–94901", J. Chem. Soc., Perkin Trans. I, (1988) pp. 3103–3111.
Blank B, Pfeiffer FR, Greenberg CM, Kerwin JF, Thyromimetics. I. The synthesis and hypocholesteremic activity of some 3'and 3',5'–Alryl and Aryl–3,5–Diiododthyronines, J Med Chem 1963, 6:554–560.
Blank B, Pfeiffer FR, Greenberg CM, Kerwin JF, Thyromimetics. II., The Synthesis and Hypocholesteremic Activity of Some b–Diethylaminoethyl esters of Iodinated Thyroalkanoic Acids, J Med Chem 1963;560–563.
Leeson PD,Ellis D, Emmett JC, Shah VP, Showell GA, Underwood AH, Thyroid Hormone Snalogues. Synthesis of 3'–Substituted 3,5–Diiodo–L–Thyronines and Quantitative Structure–Activity Studies of in Vitro and in Vivo Thyromimetic Activities in Rat Liver and Heart, J Med Chem 1988;31:37–54.
Hamilton MA, Stevenson LM, Fonarow GC, Steimle A, Goldhaber JI, Child JS, Chopra IJ, Moriguchi JD, Hage A. Safety and hemodynamic effect of Intravenous triiodothyronine in advanced congestive heart failur, Am J Cardiol 1998;81:443–447.
Moruzzi P, Doria E, Agostoni PG, Capacchione V, Sganzerla PG, Usefulness of L–Thyroxine to improve Cardiac and Exercise Performance in Dilated Cardiomyopathy, Am J Cardiol 1994; 73:374–78.
Moruzzi, P, Doria E, Agostoni PG, Medium–Term Effectiveness of L–Thyroxine Treatment in Idiopathic Dilated Cardiomyopathy, Am J Med 1996; 101:461–467.
Pennock GD, Raya TE, Bahl JJ, Goldman S, Morkin E, Cardiac Effects of 3,5–Diiodothyropropionic Acid, a Thyroid Hormone Analog with Inotropic Selectivity, J. Pharmaco Exp Ther 1992;263:163–69.
Mahaffey KW, Raya TE, Pennock GD, Morkin E, Goldman S., Left Ventricular Performance and Remodeling in Rabbits After Myocardial Infarction. Effects of a Thyroid Hormone Analogue, Circulation 1995;91:794–801.
Pennock GD, Raya TE, Bahl JJ, Goldman S. Morkin E., Combination Treatment with Captopril and the Thyroid Hormone Analogue, 3,5–Diiodothyropropionic Acid. A New Approach to Improving Left Ventricular Performance in Heart Failure Circulation 1993;88:1289–98.

(List continued on next page.)

Primary Examiner—Alan L. Rotman
Assistant Examiner—Taylor V Oh
(74) Attorney, Agent, or Firm—Hayes Soloway P.C.

(57) ABSTRACT

A method for treating a patient having congestive heart failure by administering a therapeutically effective amount of 3',3,5-triiodothyropropionic acid (TRIPROP) or 3,5,3',5'-tetraiodothyropropionic acid (TETRAPROP). Also described is a method to lower cholesterol blood levels of a patient by administering a therapeutically effective amounts of TRIPROP or TETRAPROP.

20 Claims, No Drawings

OTHER PUBLICATIONS

Goldman S, Olajos M, Morkin E., Control of Cardiac Output in Thyrotoxic Calves. Evaluation of Changes in Systemic Circulation, J Clin Invest 1984;73:358–65.

Asanoi H, Ishizaka S, Joho S, Kameyama T, Inou H, Sasayama S., Altered Inotropic and Lusitropic Responses to Heart Rate in Conscious Dogs with Tachycardia Induced Heart Failure, J Am Coll Cardiol 1996;27:728–35.

Mulleri LA, Hasenfuss G, Leavitt B, Allen PD, Alpert NR, Altered Myocardial Force–Frequency Relation in Human Heart Failure, Circulation 1992;85:1743–50.

13. Litwin SE, Zhang D, Roberg P, Pennock GD., DITPA Prevents the Blunted Contraction–Frequency Relationship in Myocytes from Infarcted Hearts, Am J Physiol (Heart and Circ Physiol) 2000;278:H862–70.

Khoury SF, Hoit BD, Vrushank D, Pawloski–Dahm CM, Shao Y, Gabel M, Periasamy M, Walsh RA, Effects of Thyroid Hormone on Left Ventricular Performance and Regulation of Contractile Ca2+Cycling Proteins in the Baboon. Implications for the Force–Frequency and Relaxation–Frequency Relationship, Cir Res. 1196;79:727–35.

Hoit BD, Pawsloski–Dahm CM, Shao Y, Gabel M, Walsh RA, The Effects of a Thyroid Hormone Analog on Left Ventricular Performance and Contractile and Calcium Cycling Proteins in the Baboon, Proc Assoc Am Physicians 1997; 109:136–45.

Tomanek RJ, Zimmerman MB, Survarna PR, Morkin E, Pennock GD, Goldman S., A Thyroid Hormone Analog Stimulates Angiogenesis in the Post Infarction Rat Heart, J Mol Cell Cardiol 1998;30:925–32.

Matsuura T., Synthesis of 3,5,3',5'Hhalogen–Substituted ThyropropionicAacids, J Med Chem 1964;830–831.

\* cited by examiner

METHOD TO TREAT CHRONIC HEART FAILURE AND/OR ELEVATED CHOLESTEROL LEVELS

CROSS REFERENCE TO RELATED APPLICATION

This application is a Continuation-in-Part of U.S. application Ser. No. 09/774,994, filed Jan. 31, 2001 now U.S. Pat. No. 6,534,676.

FIELD OF THE INVENTION

The present invention relates to a treatment for patients having congestive heart failure and/or elevated cholesterol blood levels.

BACKGROUND OF THE INVENTION

Congestive heart failure continues to be a major health problem, affecting about 4.6 million people in the United States, and its prevalence is predicted to increase over the next several decades. The magnitude of heart failure as a clinical problem has placed emphasis on the need to develop new treatment strategies.

One approach that has emerged is the use of thyroid hormone, which has unique physiologic and biochemical actions that make it a novel and potentially useful agent for treatment of heart failure. Thyroid hormone has been shown to act at the transcriptional level on the content of myocardial calcium cycling proteins to stimulate calcium uptake by sarcoplasmic reticulum. In addition, thyroid hormone causes a reciprocal shift in cardiac myosin heavy chain (MHC) isoform expression, increasing the expression of the high activity $V_1$ isoform and decreasing the low activity $V_3$ form. These biochemical alterations may underlie the ability of thyroid hormone to increase the rates of ventricular pressure development and relaxation.

Thyroid hormones include the L-forms of thyroxine (3,5, 3'5'-L-thyronine; hereinafter thyroxine or $T_4$) and triiodothyronine (3',3,5-L-triiodothyrone; hereinafter triiodothyronine or $T_3$). 3',5',3-L-Triiodothyronine (hereinafter Reverse $T_3$ or r $T_3$), is a normal metabolite of $T_4$. $T_4$ is synthesized in the thyroid gland and is the circulating form of hormone found in plasma. Although small amounts of $T_3$ are synthesized by the thyroid gland, the majority is formed from the metabolism of thyroxine in peripheral tissues by the enzyme 5'-monodeiodinase. The molecular basis for the actions of thyroid hormones is though to be mediated through the binding of $T_3$ to chromatin-bound nuclear receptors. There are two major subtypes of the thyroid hormone receptor, TR$\alpha$ and TR$\beta$, which are the products of two different genes. These genes are members of the c-erbA protooncogene family and are related to a large number of steroid and peptide hormone receptors collectively known as the steroid-thyroid hormone superfamily. The TR $\alpha$ and $\beta$ subtypes are differentially expressed in various tissues.

Thyroxine, synthesized by methods such as described in U.S. Pat. No. 2,803,654, is the principle thyroid hormone in current clinical use. This is largely because of its long half-life of 6–7 days. Triiodothyronine, which is less strongly bound to plasma proteins and has a more rapid onset of action, is available for intravenous administration. However, $T_3$ has a relatively short half-life of two days or less.

Numerous studies have been carried out to synthesize thyroid hormone analogs that mimic the actions of the natural hormones. The objective of most of these. efforts has been to develop thyromimetics that lower plasma cholesterol without adverse cardiac effects. A series of thyroxine analogs and methods of synthesis are described in U.S. Pat. No. 3,109,023.

Thyroid hormone agonists that are highly selective for the thyroid hormone receptor $\beta$ subtype are described in U.S. Pat. No. 5,883,294. U.S. Pat. No. 5,284,971 describes a class of thyromimetics, which have the distinguishing characteristic of a sulfonyl bridge in the diphenyl core.

A more recent development has been the use of thyroid hormones for the treatment of cardiovascular compromise. A method for the treatment of patients with sudden (acute) cardiovascular compromise by administration of thyroid hormone is described in U.S. Pat. No. 5,158,978. The method teaches administration of $T_4$ and $T_3$ after cardiac arrest by injection into a vein, a central venous catheter, into the pulmonary circulation or directly into the heart.

Short-term intravenous administration of $T_3$ to patients with advanced congestive failure has been shown to improve cardiac output and decrease arterial vascular resistance. Oral administration of L-thyroxine also has been shown to improve cardiac performance and exercise capacity in patients with idiopathic dilated cardiomyopathy when given for two weeks and 3 months. Although the number of patients in these studies was small, the results were generally favorable and established the basis for further investigation into the safety and potential benefits of treatment of heart failure with thyroid hormone or thyroid hormone analogs.

In addition to its well-known chronotropic and inotropic actions on the heart, thyroid hormone decreases arterial resistance, venous resistance and venous compliance. The net effect of these changes is to increase cardiac output more than arterial pressure, resulting in decreased calculated arterial vascular resistance.

Because of potential adverse effects of thyroid hormone, such as metabolic stimulation and tachycardia, what is required are thyroid hormone analogs with fewer undesirable side effects. In our above identified co-pending application Ser. No. 09/774,994, we describe the use of 3,5-diiodothyropropionic acid (DITPA), a thyroid hormone analog, for treating patients with congestive heart failure. Like thyroid hormone, DITPA binds to nuclear $T_3$ receptors of the c-erbA proto-oncogene family. DITPA has been shown to improve left ventricular (LV) performance in post-infarction experimental models of heart failure when administered alone or in combination with an angiotensin I-converting enzyme inhibitor, with approximately half of the chronotropic effect and less metabolic stimulation than L-thyroxine.

As reported in our aforementioned application, when used in experimental models of heart failure, DITPA acts similarly to thyroid hormone, affecting both the heart and the peripheral circulation. Loss of the normal increase in contractility with heart rate, referred to as the positive force-frequency relationship, has been reported both in failing human myocardium and in animal models of heart failure. DITPA administration prevents the flattened contraction-frequency relationship in single myocytes from infarcted rabbit hearts. DITPA improves myocyte function, enhances calcium transport in the sarcoplasmic reticulum (SR) and prevents the down regulation of SR proteins associated with post-infarction heart failure in rabbits. In normal primates, DITPA enhances the in vivo force-frequency and relaxation-frequency relationships in a manner similar to thyroid hormone. DITPA is able to bring about these hemodynamic changes without increasing cardiac mass appreciably or adversely affecting ventricular dimensions. A morphometric analysis indicates that in post-infarction rats treated with DITPA there is an increase in capillary growth in the border zone around the infarct.

BRIEF DESCRIPTION OF THE INVENTION

Having demonstrated the utility of DITPA for treating patients with congestive heart failure, we set about to identify other DITPA-like compounds having similar utility. We found that two more of the iodination propionic derivatives, namely the triiodo derivative 3',3,5-triiodothyropropionic acid (or "TRIPROP") and the tetraiodo derivative, 3,5,3',5'-tetraiodothyropropionic acid (or "TETRAPROP") have been identified as having thyromimetic effects in experimental studies[1] and were effective clinically in reducing serum cholesterol without increasing basal metabolic rate (BMR)[2]. These properties make them similar to DITPA in terms of the ability to treat congestive heart failure.

[1]Money W. L., Meltzer R. I., Feldman D., Rawson R. W.: The Effects of Various Thyroxine Analogues on Suppression of $^{131}$I Uptake by the Rat Thyroid, Endocrinology 64:123–125 (1959); Stasilli N. R., Kroc R. L., Meltzer R. I.: Antigoitrogenic and Calorigenic Activities of Thyroxine Analogues in Rats, Endocrinology 64:62–82 (1959).
[2]Leeper R. D., Mead A. W., Money W. L., Rawson R. W.: Metabolic Effects and Therapeutic Applications of Triiodothyropropionic Acid, Clin Pharmacol Ther 2:13–21, 1961; Hill S. R., Jr., Barker S. B., McNeil J. H., Tingley J. O., Hibbett L. L.: The Metabolic Effects of the Acetic and Propionic Acid Analogs of Thyroxine and Triiodothyronine. J. Clin. Invest. 39:523–533, 1960.

DETAILED DESCRIPTION OF THE PREFERRED EMBODIMENTS

In overview, TRIPROP and TETRAPROP may be synthesized following the teachings of Tomita and Lardy[3] by iodination of diiodothyropropionic acid (DITPA) as follows. In the case of TRIPROP, a solution of 150 mg of DITPA in 150 ml of methanol and 70 ml of concentrated aqueous ammonium hydroxide was iodinated with 4.3 ml of 1 N iodine while being stirred in an ice bath (0–2° C.). The color of iodine disappeared in about 15 min. After evaporating the colorless reaction mixture in vacuo the residue was washed with water acidified with acetic acid and recrystallized from absolute ethanol; m.p. 200° C., yield 50 mg. TETRAPROP may be similarly prepared using a stoichiometric excess of iodine. DITPA was synthesized by the method of Wawzonek et al. (1950)[4.] 3,5 diiodo-4-(4'-methoxyphenoxy) phenylacrylic acid was prepared by condensing 3,5-diiodo-4-(4'-methoxyphenoxy)benzaldehyde with malonic acid in the presence of pyridine and piperidine. DITPA was then prepared from 3,5-diiodo-4-(4'-methoxyphenoxy) phenylacrylic acid by treatment with hydriodic acid and red phosphorus in acetic anhydride. TETRAPROP and TRIPROP also may be prepared by reacting ethyl-3-(3,5-diiodo-4-hydroxyphenyl)propionate and dianisoleiodonium bromide to obtain the product acid, DITPA, following the teachings of Matsuura[5]. DITPA may then be iodinated as described by Tomita and Lardy as above reported.

[3]Tomita K., Lardy H. A., Synthesis and Biological Activity of Some Triiodinated Analogues of Thyroxine. J. Biol Chem 219:595–604 (1956).
[4]Wawzonek, S. Wang S C, Lyons P. The preparation of thyroxine analogs. J Org Chem 15:593–599 (1950).
[5]Matsuura T. Synthesis of 3,5,3',5' Halogen-Substituted Thyropropionic Acids. J. Med. Chem. 7:830–831 (1964).

Prior to administration to either human patients, or to animals, the TRIPROP or TETRAPROP, as the case may be, is then dispersed or dissolved in a pharmaceutically acceptable carrier and, if desired, further compounded with one or more ingredients selected from a stabilizer, an excipient, a solubilizer, an antioxidant, a pain-alleviating agent, an isotonic agent, and combinations thereof.

The TRIPROP and the TETRAPROP of the present invention may be formulated as a liquid preparation, e.g., for parenteral administration intravenously, subcutaneously or intramuscularly, or intranasally or orally, as a solid preparation for oral administration, e.g., pills, tablets, powders, or capsules, as an implant preparation, or as a suppository for rectal administration. For example, the formulation for parenteral administration for injection may be prepared by conventional methods known to a person skilled in the art, such as by dissolving the TRIPROP or TETRAPROP in an appropriate solvent or carrier such as sterilized water, buffered solution, isotonic sodium chloride solution and the like, and may be formulated as solutions, emulsions or suspensions. For rectal administration, a unit dose of TRIPROP or TETRAPROP may be formulated with cocoa butter or a glyceride.

TRIPROP or TETRAPROP also may be administered in the form of inhalation or insufflation. For administration by inhalation or insufflation a solution of TRIPROP or TETRAPROP is conveniently delivered in the form of an aerosol spray presentation from pressurized packs or nebulizer, with the use of suitable propellants such as carbon dioxide or other suitable gasses. In addition, TRIPROP or TETRAPROP may. be administered using other conventional drug delivery systems well known to a person skilled in the art. Examples of the preparations for drug delivery system are microspheres (nanoparticle, microparticle, microcapsule, bead, liposome, multiple emulsion, etc.) and the like.

A stabilizer may be added to the formulation, and the examples of a stabilizer include albumin, globulin, gelatin, mannitol, glucose, dextran, ethylene glycol and the like. The formulation of the present invention may include a necessary additive such as an excipient, a solubilizer, an antioxidant agent, a pain-alleviating agent, an isotonic agent and the like. The liquid formulation may be stored in frozen condition, or after removal of water by a process such as freeze-drying. The freeze-dried preparations are used by dissolving in pure water for injection and the like before use.

For treating congestive heart failure, the TRIPROP according to the present invention can be administered at doses between 0.014 and 0.056 mg/kg, or 1 to 4 mg per day for a 70 kg person. Doses of TETRAPROP can be administered at 0.171 mg/kg or 12 mg per day for a 70 kg person.

Effective dosages and schedules for administering TRIPROP or TETRAPROP may be determined empirically by measuring serum thyrotropin levels and monitoring for signs and symptoms of hyper- or hypothyroidism. An administration route of the preparation may vary depending on the form of preparation. For example, the parenteral preparation may be administered intravenously, intraarterially, subcutaneously or intramuscularly.

In addition, TRIPROP or TETRAPROP also may be formulated for transdermal or implant administration. Such long acting implantation administrations include subcutaneous or intramuscular implantation. Thus, for example, TRIPROP or TETRAPROP may be formulated with suitable polymeric or hydrophobic materials (for example as an emulsion in an acceptable oil) or ion exchange resins or as sparing soluble derivatives, for example as a sparingly soluble salt.

A suitable transdermal delivery system includes a carrier, such as a liquid, gel, solid matrix, or pressure sensitive adhesive, into which TRIPROP or TETRAPROP is incorporated. In one embodiment, no backing material is present. In an alternative embodiment, backing may be used in combination with a carrier. In this later embodiment, portions of the carrier that are not in physical contact with the skin or mucosa may be covered with a backing, which serves to protect the carrier and the components contained in the carrier, including the TRIPROP or TETRAPROP being delivered, from the environment. Backings suitable for such use include metal foils, metalized plastic films, and single layered and multilayered polymeric films.

For transdernal delivery of TRIPROP or TETRAPROP, the TRIPROP or TETRAPROP is dissolved in a solvent system. A suitable solvent system includes water, and optionally one or more lower alcohols such as ethanol, isopropyl alcohol, propyl alcohol, and the like. Preferably, such alcohols have carbon contents between 2 and about 6. The solvent system may additionally include a glycol such as ethylene glycol, propylene glycol, glycerol, and the like. The solvent system also may include one or more dialkylsulfoxides and/or dialkylsulfones, and/or one or more ketones, ethers, and esters, such as acetone, methylethylketone, dimethylether, diethylether, dibutylether, and alkyl acetates, alkyl proprionates, alkyl butyrates, and the like.

Although solutions of TRIPROP and TETRAPROP are preferred, emulsions may be used. Such emulsions may be aqueous, wherein the aqueous phase is the major and continuous phase, or non-aqueous, wherein a water-insoluble solvent system comprises the continuous phase.

As with DITPA of our parent application, the transdermal delivery of TRIPROP or TETRAPROP is effective to treat chronic heart failure and/or lower LDL-cholesterol levels even without including a substance capable of in vivo stimulation of adenosine 3',5'-cyclic monophosphate, and even without including a substance capable of in vivo stimulation of guanosine 3',5'-cyclic monophosphate. If desired, substances such as an extract of Coleus Forskholi, optionally may be included in the transdermal delivery TRIPROP and TETRAPROP formulations at a level of between about 0.0001 weight percent to about 1.0 weight percent.

The transdermal delivery TRIPROP and TETRAPROP formulations also may contain agents known to accelerate the delivery of medicaments through the skin or mucosa of animals, including humans. These agents are sometimes known as penetration enhancers, accelerants, adjuvants, and sorption promoters, and are collectively referred to herein as "enhancers." Some examples of enhancers include polyhydric alcohols such as dipropylene glycol; oils such as olive oil, squalene, and lanolin; polyethylene glycol ethers and fatty ethers such as cetyl ether and oleyl ether; fatty acid esters such as isopropyl myristate; fatty acid alcohols such as oleyl alcohol; urea and urea derivatives such as allantoin; polar solvents such as dimethyldecylphosphoxide, methyloctylsulfoxide, dimethylacetonide, dimethyllaurylamide, dodecylpyrrolidone, isosorbitol, decylmethylsulfoxide, and dimethylformamide; salicylic acid; benzyl nicotinate; bile salts; higher molecular weight aliphatic surfactants such as lauryl sulfate salts. Other agents include oleic acid and linoleic acids, ascorbic acid, panthenol, butylated hydroxytoluene, tocopherol, tocopheryl acetate, tocopheryl linoleate, propyloleate, isopropyl palmitate, oleamide, polyoxyethylene lauryl ether, polyoxyethylene olelyl ether and polyoxyethylene oleyl ether. In this embodiment, these skin penetration enhancers are present from about 0.01 weight percent to about 5 weight percent.

The transdermal TRIPROP and TETRAPROP formulations delivery system of the invention can be prepared using conventional methods to apply an appropriate carrier to an appropriate backing. For example, a TRIPROP or TETRA-PROP-in-adhesive device can be prepared by preparing a coating formulation by mixing a solution of the adhesive in a solvent system containing TRIPROP or TETRAPROP, and any other desired components, to form a homogeneous solution or suspension; applying the formulation to a substrate such as a backing or a release liner; using well known knife or bar or extrusion die coating methods; drying the coated substrate to remove the solvent; and laminating the exposed surface to a release liner or backing.

The following examples illustrate pharmaceutical compositions according to the present invention.

EXAMPLE 1

A solution of TRIPROP is prepared following the procedure described by Tomita and Lardy as above reported by iodination of DITPA as follows. A solution of 150 mg of DITPA in 150 ml of methanol and 70 ml of concentrated aqueous ammonium hydroxide was iodinated with 4.3 ml of 1 N iodine while being stirred in an ice bath (0–2° C.). The color of iodine disappeared in about 15 minutes. After evaporating the colorless reaction mixture in vacuo the residue was washed with water acidified with acetic acid and recrystallized from absolute ethanol; m.p 200° C., yield 50 mg.

The resulting solution of TRIPROP was mixed with lactose and packed into gelatin capsules containing 1–2 mgs of the active ingredient per capsule.

EXAMPLE 2

TRIPROP was prepared as in Example 1. However, the resulting solution was lyophilized and packaged in individual ampules containing 1–2 mgs of the active ingredient per capsule.

EXAMPLE 3

TRIPROP was prepared as in Example 1. The active compound was isolated and blended with gelatin, polyvinylpyrrolidone, starch, talc and sodium benzoate to form a waxy matrix to slow the absorption of TRIPROP. The resulting blend was divided and loaded into gelatin capsules, each containing 1–4 mgs of the active ingredient per capsule.

EXAMPLE 4

TRIPROP was prepared as in Example 1. The active compound was isolated and solubilized in methanol. The resulting blend was coated on a porous patch, each patch containing 1–4 mgs of the active ingredient per patch, and allowed to dry.

EXAMPLES 5–8

Examples 1–4 were repeated, using TETRAPROP prepared either by the method of Tomita and Lardy[3] or Matsuura[5].

While the invention has been described in detail herein in accordance with certain preferred embodiments thereof, many modifications and changes therein may be effected by those skilled in the art. Accordingly, it is intended by the appended claims to cover all such modifications and changes as fall within the true spirit and scope of the invention.

I claim:

1. A method for treatment of a patient with congestive heart failure, comprising administering to the patient a therapeutically effective amount of 3',3,5-triiodothyropropionic acid or 3,5,3',5'-tetraiodothyropropionic acid.

2. The method of claim 1, wherein 3',3,5-triiodothyropropionic acid or 3,5,3',5'-tetraiodothyropropionic acid is administered as a formulation selected from the group consisting of a liquid preparation, solid preparation, capsule preparation, and an implant preparation.

3. The method of claim 2, wherein said formulation further comprises a pharmaceutically acceptable carrier.

4. The method of claim 3, wherein said formulation further comprises at least one of a stabilizer, excipient, solubilizer.

5. The method of claim 1, wherein said 3',3,5-triiodothyropropionic acid or 3,5,3',5'-tetraiodothyropropionic acid is administered by parenteral injection.

6. The method of claim 5, wherein said 3',3,5-triiodothyropropionic acid or 3,5,3',5'-tetraiodothyropropionic acid is administered by parenteral intravenous injection.

7. The method of claim 1, wherein said 3',3,5-triiodothyropropionic acid or 3,5,3',5'-tetraiodothyropropionic acid is administered orally.

8. The method of claim 1, wherein said 3',3,5-triiodothyropropionic acid or 3,5,3',5'-tetraiodothyropropionic acid is administered directly to the pulmonary system of the patient.

9. The method of claim 1, wherein said 3',3,5-triiodothyropropionic acid or 3,5,3',5'-tetraiodothyropropionic acid is administered transdermally.

10. The method of claim 1, wherein said 3',3,5-triiodothyropropionic acid or 3,5,3',5'-tetraiodothyropropionic acid is administered by implantation.

11. A method to lower cholesterol blood levels of a patient, comprising administering to the patient a therapeutically effective amount of 3',3,5-triiodothyropropionic acid or 3,5,3',5'-tetraiodothyropropionic acid.

12. The method of claim 11, wherein 3',3,5-triiodothyropropionic acid or 3,5,3',5'-tetraiodothyropropionic acid is administered as a formulation selected from the group consisting of a liquid preparation, solid preparation, capsule preparation, and an implant preparation.

13. The method of claim 12, wherein said formulation further comprises a pharmaceutically acceptable carrier.

14. The method of claim 13, wherein said formulation further comprises at least one of a stabilizer, excipient, solubilizer.

15. The method of claim 11, wherein said 3',3,5-triiodothyropropionic acid or 3,5,3',5'-tetraiodothyropropionic acid is administered by parenteral injection.

16. The method of claim 15, wherein said 3',3,5-triiodothyropropionic acid or 3,5,3',5'-tetraiodothyropropionic acid is administered by parenteral intravenous injection.

17. The method of claim 11, wherein said 3',3,5-triiodothyropropionic acid or 3,5,3',5'-tetraiodothyropropionic acid is administered orally.

18. The method of claim 11, wherein said 3',3,5-triiodothyropropionic acid or 3,5,3',5'-tetraiodothyropropionic acid is administered directly to the pulmonary system of the patient.

19. The method of claim 11, wherein said 3',3,5-triiodothyropropionic acid or 3,5,3',5'-tetraiodothyropropionic acid is administered transdermally.

20. The method of claim 11, wherein said 3',3,5-triiodothyropropionic acid or 3,5,3',5'-tetraiodothyropropionic acid is administered by implantation.

* * * * *